United States Patent
Torrent López et al.

[11] Patent Number: 5,758,367
[45] Date of Patent: Jun. 2, 1998

[54] LUMBAR PROTECTOR WITH UNDERPANTS INCORPORATED

[76] Inventors: Eva Torrent López, P$_o$ Valldoreix, 90, Sant Cugat Del Valles (Barcelona), Spain, 08190; Patricia Torrent López, P$_o$ Valldoreix 90, Sant Cugat Del Valles (Barcelona), Spain, 08940

[21] Appl. No.: 662,867

[22] Filed: Jun. 12, 1996

[30] Foreign Application Priority Data

Feb. 1, 1996 [ES] Spain ................ 9600307

[51] Int. Cl.$^6$ .................................. A41B 9/00
[52] U.S. Cl. .................. 2/400; 2/406; 2/403; 450/155
[58] Field of Search ............... 2/400–408, 227, 2/228, 220, 221, 236, 237, 238; 450/155, 97–99

[56] References Cited

U.S. PATENT DOCUMENTS

| | | | |
|---|---|---|---|
| 2,130,906 | 9/1938 | Scherfer | 2/406 |
| 2,602,928 | 7/1952 | Chatfield | 2/234 |
| 2,792,698 | 5/1957 | Hampp | 2/401 |
| 3,083,710 | 4/1963 | Rauser | 2/401 |
| 3,174,482 | 3/1965 | Parrott | 450/155 |
| 4,642,818 | 2/1987 | Dehnert et al. | 2/400 |

*Primary Examiner*—Gloria Hale
*Attorney, Agent, or Firm*—Richard M. Goldberg

[57] ABSTRACT

Lumbar protector with underpants incorporated, including a pair of underpants; and a closed band sewn to an upper part of the pair of underpants and having a band height such that the band covers at least lumbar vertebrae of a user, the band being produced in natural textile fibers with a significant caloric effect and at least ten per cent selected from the group consisting of elastomeric polyurethane, rubber and similar fibers, and the lumbar protector has either natural colors of the fiber, or colors from treatment with natural dyes.

3 Claims, 2 Drawing Sheets

5,758,367

LUMBAR PROTECTOR WITH UNDERPANTS INCORPORATED

BACKGROUND OF THE INVENTION

This invention refers to a lumbar protector with underpants incorporated, especially designed for the comfort of individuals who suffer from discomfort in the lumbar area of the body. It improves the condition of these individuals enormously, and constitutes a product whose hygienic and utilitarian characteristics are much better than those of any other product for the same or similar purposes currently available on the market.

One of the groups of people for whom the lumbar protector which forms the basis of the present invention has been especially developed, are those who suffer from lumbago, a disease which generates considerable pain in the lumbar region. It can be improved using systems which provide heat in the said region, including massage, currents, laser systems, etc., as well as certain types of girdles which encircle and compress the said region, achieving a temperature which reduces the paint and remaining securely in plate, benefitting the patients However, the girdles commonly used for this purpose on the market present significant drawbacks, well known to their users. These drawbacks may be classified in two groups:

1) Since the girdle is another item worn by the person, separate from other clothes, it tends to move and consequently rolls on itself or ends up in positions which are very uncomfortable for the user.

2) These girdles are produced in rubber or similar materials, and it is therefore very complicated to keep them in hygienic conditions, since they are not easy to wash and the do not allow any transpiration. From this point of view, therefore they are not to be recommended, and they may even cause problems of allergy due to the material with which they are produced.

SUMMARY OF THE INVENTION

The lumbar protector with underpants incorporated, which constitutes the basis of the present invention, comprises a fundamental change against the products used for this purpose on the market, It basically consists of a protector for the lumbar region, produced in natural fibres with the addition of elastomeric polyurethane, rubber or similar fibres in a proportion of no less than 10%. The width of the resulting band enables at least the lumbar vertebrae to be covered. The band is produced in a material that enables it to be joined by a simple sewing process to a conventional pair of underpants, yielding a single article of clothing which serves as underpants at the lower part, while the upper part is extended in the form of a wide band with the characteristics described above. The latter, given the materials employed in its production, provides considerable advantages for individuals with lumbar problems. The said advantages can be classified as follows:

A. Protection, since it produces heat and prevents cold, thus reducing the pain, confining the lumbar and abdominal region and keeping it relaxed and warm.

B. Comfort, since it enables users to see to their biological needs without the psychological trauma often produced by the knowledge that conventional orthopaedic elements such as the girdles mentioned above are used, since this is a product which is worn in exactly the same way as a conventional pair of underpants, with a fine, soft and pleasant feel C. Hygiene, since it can be washed daily with no short term deterioration of the natural fibres it comprises, just as with conventional underwear.

D. Hypoallergenic, since the natural fibres and materials with which it is produced, prevent allergy and irritation of the skin.

E. Colour, which may be varied, although only the natural colours of cotton or dyes which pose no problems to the health will be used, so that the existence of different colour options will not lead to any allergies.

The basic differentiating characteristic of the lumbar protector with respect to current girdles is the fact that it is made in natural fibres mixed with at least 10% elastomeric polyurethane, rubber or similar fibres, with natural colours, producing a closed band of a certain degree of elasticity which is subsequently sewn to conventional underpants.

The natural fibres may be of the cotton, wool or viscose type, the only essential consideration for the purposes of the present invention being that they must provide the caloric level required for the functional purpose described.

It is self-evident that incorporation of the said lumbar protector to women's underpants or tights as opposed to men's underpants does not affect the principles of the invention in any way, since the characteristics indicated herein may be applied to all the above products, so that this possibility is fully covered by the general object of the present application.

We can therefore specify that the present lumbar protector is especially conceived for use by men or women who suffer from lumbago, malformations or malpositions of the spinal column, rheumatic diseases of the vertebrae (lumbar spondylarthritis and spondylarthrosis), osseous lesions of the vertebral column due to tumours, osteoporosis, reflexes of kidney and/or intestinal disease, pathological alterations of the intervertebral discs, hernia of the intervertebral discs, menstrual pain in some women, gynaecological diseases, pinching, and specific situations occuring in sportspersons and pregnant women.

BRIEF DESCRIPTION OF THE DRAWINGS

In order to facilitate comprehension of the explanation, a page of drawings is enclosed with the present statement, by way of illustration and not being in any way restrictive, representing several examples of lumbar protectors with underpants incorporated, according to the principles set forth in the claims.

In the drawings.

DETAILED DESCRIPTION

Figure 1:
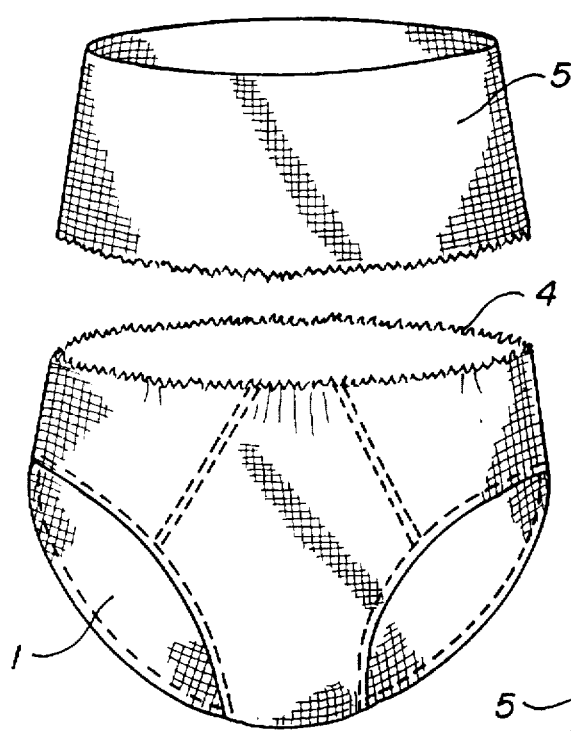
FIGS. 1 and 2 both show perspective views of a lumbar protector with underpants incorporated, the first with the component parts still separate, and the second with the component parts joined together.
Figure 2:
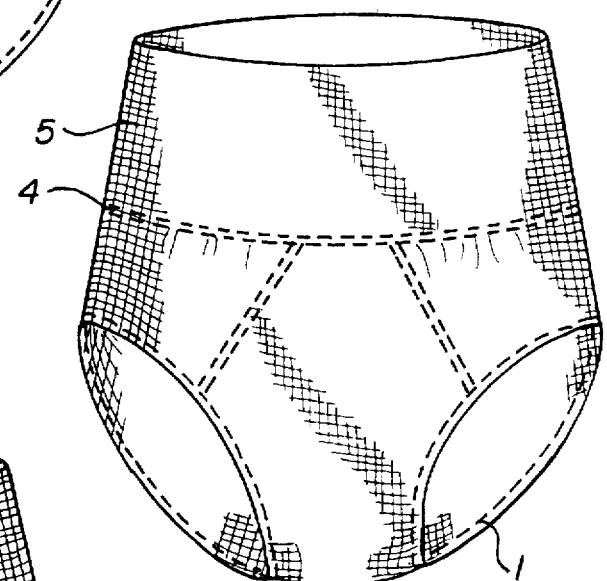
Figure 3:
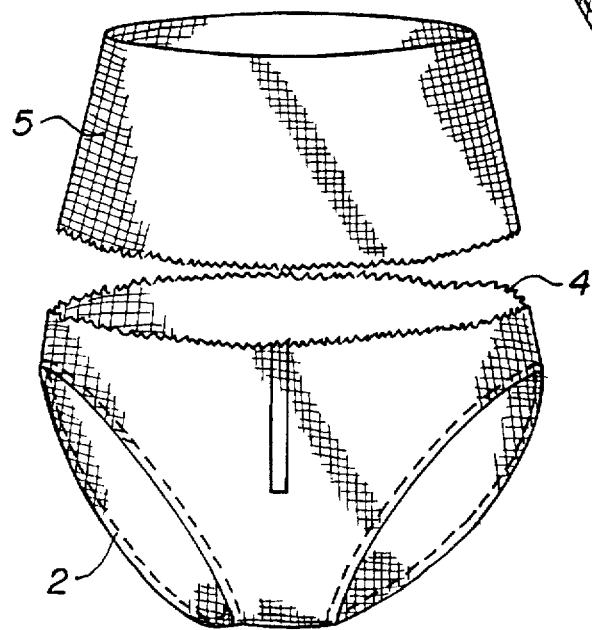
FIGS. 3, 4, 5 and 6 represent two pairs of views, as in the first two diagrams, of another two figures in which the said lumbar protector is joined to women's underpants or tights respectively
Figure 4:
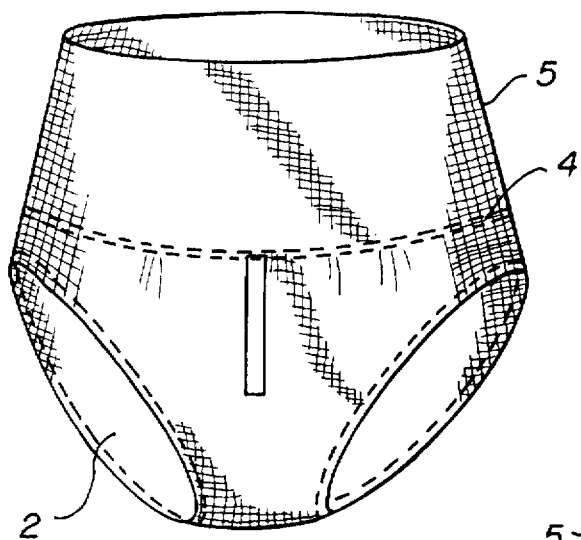
Figure 5:
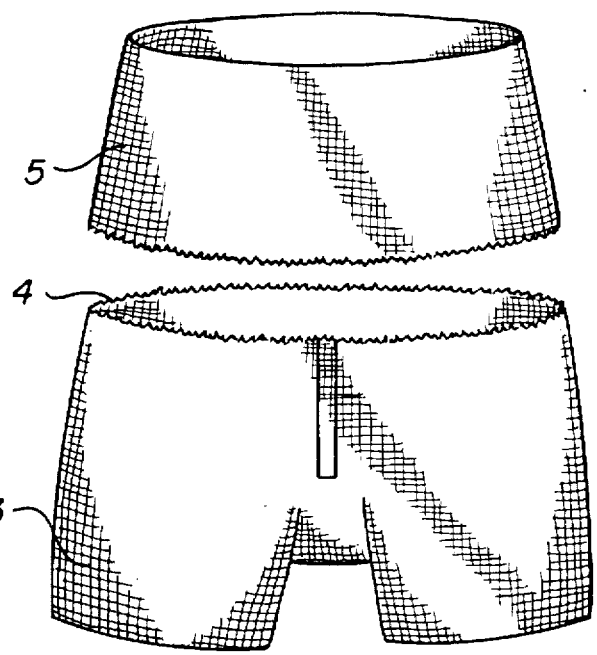
Figure 6:
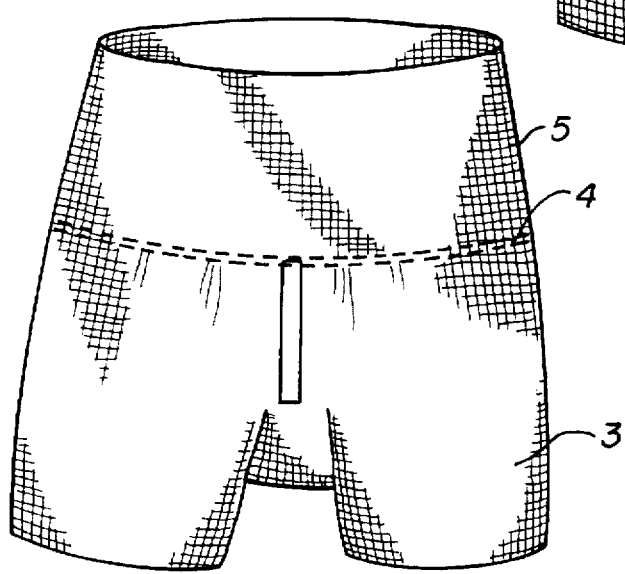

As one can deduce from said drawings, the invention comprises joining conventional men's underpants -1-, women's underpants -2- or tights -3-, using a normal sewing system -4- such as that commonly used in the production of the said articles of clothing, to a lumbar protector -5- which adopts the form of a closed surface of sufficient width to cover the different lumbar vertebrae of the user. The said protector is woven in natural textile fibres which provide heat, with at least 10% elastomeric polyurethane, rubber or similar fibres. The natural colours of the sails fibres or other dyes produced in a natural process which do not damage the health, may be used in the finish. By using the lumbar protector with underpants incorporated which constitutes the basis of the present invention, any man or woman suffering from any of the conditions described above will be able to significantly relieve their discomfort, using an article of clothing which will in no case make them feel any differences with respect to their conventional underwear, apart from increased pressure in the lumbar region. This will be welcomed due to the improved comfort, and the pressure will go hand in hand with increased heat in the said region up to the height desired. Allergic reactions to this article of clothing need not be feared in any case, and it can be used with the same levels of hygiene as those achieved with conventional underwear.

All that does not affect, alter, change or modify the essence of the lumbar protector described herein which may be varied in the present invention.

We claim:

1. Lumbar protector with underpants incorporated, comprising:

a pair of underpants; and a closed band sewn to an upper part of the pair of underpants and having a band height such that said band covers at least all lumbar vertebrae of a user, said closed band having a substantially cylindrical configuration with a circumferential lower edge that is substantially in the same plane, said band being produced in natural textile fibers with a significant heating effect and at least ten per cent selected from the group consisting of elastomeric polyurethane, rubber and similar fibers, and the lumbar protector having one of:

natural colors of the fiber, and colors from treatment with natural dyes.

2. The lumbar protector with underpants incorporated, according to claim 1, wherein said natural textile fibers are selected from the group consisting of cotton, wool and viscose type materials.

3. The lumbar protector with underpants incorporated, according to claim 1, wherein said band height is of a sufficient height so that said band covers an entire lumbar region of a user.

* * * * *

UNITED STATES PATENT AND TRADEMARK OFFICE
CERTIFICATE OF CORRECTION

PATENT NO.   : 5,758,367
DATED        : June 2, 1998
INVENTOR(S)  : Eva TORRENT LOPEZ et al It is certified that error appears in the above-indentified patent and that said Letters Patent is hereby corrected as shown below:

```
Column 1, line 22, change "paint" to -- pain, --;
                   change "plate" to -- place --;

line 23, change "patients" to -- patient. --;

line 46, after "market" change "," to -- . --.

Column 2, line 59, after "respectively" insert -- . --.
```

Signed and Sealed this

Eleventh Day of August 1998

Attest:

BRUCE LEHMAN

Attesting Officer     Commissioner of Patents and Trademarks